United States Patent [19]
Feuerstein et al.

[11] Patent Number: 5,177,511
[45] Date of Patent: Jan. 5, 1993

[54] APPARATUS FOR PRODUCING IMAGES OF AN OBJECT AND IN PARTICULAR FOR OBSERVING THE REAR PORTIONS OF THE EYE

[75] Inventors: Manfred Feuerstein; Ulrich Klingbeil; Claus H. Kühl; Andreas Plesch, all of München, Fed. Rep. of Germany

[73] Assignee: G. Rodenstock Instruments GmbH, Fed. Rep. of Germany

[21] Appl. No.: 697,495
[22] PCT Filed: Nov. 9, 1987
[86] PCT No.: PCT/DE87/00589
§ 371 Date: Jul. 8, 1988
§ 102(e) Date: Jul. 8, 1988
[87] PCT Pub. No.: WO88/03396
PCT Pub. Date: May 19, 1988

Related U.S. Application Data

[63] Continuation of Ser. No. 216.521, Jul. 8, 1988, abandoned.

[30] Foreign Application Priority Data

Nov. 8, 1986 [DE] Fed. Rep. of Germany ....... 3638226

[51] Int. Cl.⁵ .............................................. A61B 3/10
[52] U.S. Cl. ................................. 351/205; 351/221
[58] Field of Search ............... 351/205, 221, 206, 207, 351/208; 128/303.1, 745; 606/4, 5, 6

[56] References Cited

U.S. PATENT DOCUMENTS 4,838,679 6/1989 Bille .............................. 351/221 X

Primary Examiner—Rodney B. Bovernick
Attorney, Agent, or Firm—Evenson, Wands, Edwards, Lenahan & McKeown

[57] ABSTRACT

An apparatus for producing images of an object and, in particular, for observing the rear portions of the eye by an illumination device, the light of which is focused on the object to be imaged and which preferably is provided with at least one laser. A scanning device, which produces a scanning motion of the light from the illumination device on the object to be imaged. A detector device has at least one detector which receives the light reflected from the object to be imaged an assessement and synchronization unit produces the image from the time-sequential output signal from the detector device.

It is possible to gain essential ground-laying information about the object to be imaged, e.g. the fundus of the eye, by special types of illumination and/or the analysis of the scattered back light according to the most varied criteria.

46 Claims, 3 Drawing Sheets

APPARATUS FOR PRODUCING IMAGES OF AN OBJECT AND IN PARTICULAR FOR OBSERVING THE REAR PORTIONS OF THE EYE

This is a continuation of application Ser. No. 07/216,521, filed Jul. 8, 1988 now abandoned.

BACKGROUND AND SUMMARY OF THE INVENTION

The present invention relates to an apparatus for producing images of an object and in particular for observing the rear portions of the eye.

Apparatuses for producing images of an object for observing the rear portions of the eye are well known in the art and are implemented with various equipment for producing images. By way of illustration, a number of laser-scanning cameras, laser-scanning microscopes and laser-scanning ophthalmoscopes have been proposed in medical technology.

Apparatuses of the known type have proven to be particularly advantageous when a comparatively large object has to be viewed through a small aperture arranged before the object. For example, when observing the rear portions of the eye, there arises the problem that the fundus must be illuminated and observed through the pupil of the eye and frequently through the not clear anterior media of the eye, where reflexes occur to produce image defects. Similar circumstances have been encountered in other cases of medical or technical application.

For this reason, fundus cameras have usually been employed in the past to observe the rear portions of the eye, in which the entrance pupil and the exit pupil were separated according to "GULLSTRAND" to suppress the so-called corneal reflex i.e. the part of the pupil of the eye used for the illumination surrounds ring-like the part used for observation.

Nonetheless, reflexes cannot be entirely suppressed when working with such fundus cameras. Moreover, the attainable resolution of approx. 15 µm is often insufficient.

Therefore, it has repeatedly been proposed to employ apparatuses for observing the fundus of the eye, which do not illuminate expansive areas of the fundus of the eye, but rather scan as small as possible a spot with a focused illuminating light and detect the reflected light in relation to the scanning sequence. In this regard, reference is made, by way of illustration, to "The Foundations of Ophthalmology", Vol. VII, pp. 307/308, Yr. 1962, U.S. Pat. No. 4,213,678, EP-A-0 145 563 as well as Japanese patent publications 61-5730 and 50-138822.

The apparatuses described in the aforementioned references differ from one another in the pupil separation. The Japanese patent publication 61-5730 proposes a "GULLSTRAND separation", U.S. Pat. No. 4,213,678 an inverted "GULLSTRAND pupil," and the Japanese patent publication 50-138822 adjacent pupils as illumination and observation light.

In the apparatus for observing the rear portions of the eye described in EP-A-145 563, both the illumination light beam and the observation light beam are directed via a scanning device. A "double scanning system" of this type has the advantage that the reflected beam of light can be determined by means of a stationary detector with a relatively small surface.

The apparatuses mentioned in the preceding for observing the rear portions of the eye with "scanning illumination" have in common that the resolution of the received image is determined by the size of the "focus spot" (approx. 8–12 µm) on the fundus of the eye and that the reflected light is received by a single detector with a more or less large field of view aperture for building up the image of the rear portions of the eye.

Further analysis of the returned light has not previously been considered.

The present invention is based on the recognition of the fact that apparatuses for producing images, in particular, due to special types of illumination and/or the analysis of the light scattered back according to most varied criteria permits gaining essential further groundlaying information about the object of which an image is to be made, for example the fundus of the eye, than is possible with any of the other known apparatuses.

Therefore, a primary object of the present invention is to improve an apparatus for producing images of an object hereto in such a fashion, that it is possible, by means of special types of illumination and/or the analysis of the light scattered back, to analyze the object to be imaged proceding beyond a pure image production analysis.

By way of illustration, the apparatus of the present invention permits making a spatial analysis and/or one of the polarization state of the returned light. For this purpose, the apparatus is provided with several individual detectors, which, in order to receive the light reflected from different planes and/or to receive the patchlike distribution of the intensity of the light and/or to determine the polarization state of the light conjugate to different planes or assigned to different areas of a plane or to which corresponding apertures or polarization filters are connected in a series.

In this manner, apparatus permits measuring the spatial distribution of the intensity and/or the polarization state of light reflected from the object to be imaged, by for example the rear portions of the eye. Moreover, the arrangement of the detectors in planes conjugate to the different planes of the object to be imaged makes a depth analysis of the object possible.

It is expressly made clear at this point that when in the case of the present invention it is said that the detectors have a specific form or are arranged at a specific location, it is not necessary that the detectors actually are designed accordingly; but rather it suffices if apertures for determining the field of view are arranged at the corresponding location and are connected with the detectors via light-conducting means, for example relay optics or light conductors. Such an arrangement of field-of-view-determining apertures instead of detectors is a particular feature of the "scan process" used for image build-up, in which no actual image is produced, but reflected or scattered light is received and assessed time-sequentially to the image build-up at any time in the entire space angle or the assessable space angle. Another primary object of the present invention is that light of several wavelengths, preferably the light from several lasers, is projected simultaneously onto the location of the object to be imaged. By this means varied effects can be achieved.

By way of illustration, it is possible to simulate a white light illumination in a laser scanning ophthalmoscope and deliver the ophthalmologist his "accustomed" picture of the fundus of the eye with a "representation in real color".

Moreover, with an appropriate selection of the wavelengths it is possible, by way of illustration, to determine the blood oxygen saturation level, which indicates local circulatory disturbances and of the entire system, avascular zones, etc. Furthermore, tumor analysis, visual pigment analysis, etc. are possible.

In addition, the simultaneous reception of an angio-fluorescent and a "normal" image of the fundus of the eye is possible if an Ar⁻-laser or a HeNe laser and a laser with a different wavelength are employed simultaneously.

Simultaneous implementation of light of several wavelengths, moreover, makes other interesting possibility feasible.

The depth of focus of the illumination light depends on the entrance pupil, i.e. on the size and form of the pupil for the illumination light. By way of illustration, a great depth of focus is gained with an entrance pupil designed as an inverted Gullstrand pupil as proposed in the U.S. Pat. No. 4,213,678 due to the small peripheral angle of the illumination light. On the other hand, a small depth of focus is gained when a normal Gullstrand pupil or the pupil used in EP-A-0 145 563 is employed due to the large angle enclosed by the peripheral rays.

Normally, the entrance pupil is selected corresponding to the respective intention, whereby the inverted Gullstrand pupil yields the best resolution, because the optically poorer peripheral regions of the eye are not used in it and thus the illumination light can be focused onto the smallest spot diameter.

When several sources of light are employed yielding light of different wavelengths, different entrance pupils can be used, whereby, it is particularly preferable if for light of one wavelengthan entrance pupil delivering a great depth of focus is employed and an entrance pupil delivering a small depth of focus is used for light of another wavelength. In this manner, it is possible to simultaneously receive a full overall image with high resolution and great depth of focus and a second image, which is "depth selective", whereby the selection of the different entrance and, if required, exit pupils occurs, for example, by means of a suitable wavelength selective coating of the so-called optical input coupling element (divider mirror), i.e. of the mirror separating the illumination and observation beam path. In this case, complementary pupils are received for the different wavelengths. Naturally, a different separation of the pupils by suitable means is also possible, such as by employing several divider mirrors in such a fashion that other pupil separations are also possible as complementary pupils.

The signals from the various detectors, e.g. an angio-graph image and the "normal" image can be superimposed on a monitor or presented on several monitors.

In any case, the representation of both or several images in real time or following storage can be coupled. By "coupling" it meant the known state of the art operations in image processing, by way of illustration, very revealing images are received by means of "real time superimposition" of an angiograph image and a normal image. The individual direct images or those received after processing can, of course, be presented and/or received on several observation devices simultaneously, such as monitors.

In this case, it is particularly advantageous to design the apparatus of the present invention in such a fashion that both the illumination light and the reflected light are directed via the scanning device. With such an apparatus, a simple detection light signal, which does not change its position in space, is received in a simple manner behind the scanning device.

As already explained in detail, in accordance with the present invention the spatial distribution of the reflected light can be detected and assessed. For this purpose, it is, in particular, possible to arrange detectors or field-of-view determining shutters in planes which are not conjugate to the actual plane of the object.

By way of illustration, a detector arrangement or field-of-view determining shutter is provided in a plane conjugate to the pupil of the eye to detect the distribution of the intensity of the reflected light in this plane. In this case, the individual detectors or shutter elements preferably have the shape of sectors of a circle so that the main point of the reflected light or light scattered back, or directional symmetries etc. can be determined, by means of which, by way of illustration, it is possible to draw conclusions about the surface structures.

In a further embodiment, a detector arrangement or a shutter arrangement is provided in a plane conjugate to the object to be imaged, thus, by way of illustration, conjugate to the fundus of the eye, which determines the intensity of the distribution of the reflected light in this plane.

By this exemplary means, it is possible to detect the portion of transverse scattering in the retina by analyzing the distribution of the intensity in an image plane conjugate to the retina and thereby gain information about the structure of the retina.

In addition to the spatial analysis of the reflected light, another embodiment makes it possible to analyze the polarization state of the reflected light so that an improved representation of the double-refracting nerve fiber layer of the retina is yielded compared to that of the known apparatuses.

A further embodiment, moreover, permits determining the Stokes parameters to describe the polarization characteristics by which local defects can be detected, and anistropic, i.e. directional structures of the retina, such as, for example, the nerve fiber layer can be made more prominent. Moreover, with regard to the definition of Stokes parameters, reference is made to the article "Polarization Imaging" in APPLIED OPTICS; Vol. 20, pp. 1537 ff.

Further features of the present invention make an optical structure analysis or an optical image pre-processing of the reflected light possible. The optical image pre-processing operates substantially faster than available electronic image processing systems and thereby permits making special structures of objects prominent in real time even in the case of complex filtering.

Depending on the position of the analyzing filter or the shutter, polarization states can be isolated, directional anisotropes can be selected, aberrations can be compensated for, etc. It is particularly advantageous if variable filters and/or shutters controlled by, by way of illustration, a calculator exchangeable and/or rotatable shutters as well as shutters having a gradual transmission (apodization) are provided. Such shutters are generally not simple apertures, but rather formed arrangements depending on the respective use, by way of illustration, slits, rings, combinations of quadrants or a pattern of individually controlled dots. Furthermore, the shutters may be partially mirrored glass plates, perforated mirrors, wavelength-selectively vaporized mirrors or semi-translucent mirrors. It is also possible to produce zones of different optical effects by means of appropriate design of the divider mirror.

The present invention provides a simply constructed light modulator, namely, a liquid crystal element, which can be switched area-selectively translucent or untranslucent.

Another preferred solution for accomplishing a primary object of the present invention and, in particular, a design of an apparatus for observing the rear portions of the eye, is distinguished by the fact that, in addition, marks may be projected onto the object to be observed, by such as the fundus of the eye. These marks can, by way of illustration, serve to mark areas to be treated (coagulated) or to be examined, and are produced by means of image processing in a representation which was previously made. On this point, patent application P 36 07 721.6, discusses in detail the use of image processing for treatment planning and for producing markings.

These marks may, by way of illustration, be produced by "lightening" the illumination light beam at the corresponding location. The lightening is particularly preferred when the marks are to serve for orientation and/or marking a specific area as, in any case, the spatial relationship between the "scanning beam" and the mark remains constant.

However, it is also possible to employ a light source and in particular a positioning unit to project the marks as, in that case, far as possible independence of the individual systems of each other is ensured. This construction is especially recommended if the additional beam is intended for processing purposes, such as coagulating purposes.

This positioning system can, by for example, by an acousto-optical deflector or a wobble optic shown in German patent application P 35 32 464.3, as the same is stable and easy to handle.

On the other hand, in accordance with the present invention, an x/y-scanner with a polygonal mirror drum and a galvanometer mirror is preferably used as the scanning device for a system of this type which operates independently of wavelengths, and is particularly of advantage in the case of the simultaneous implementation of light of several wavelengths.

Besides the possible applications of the additional mirrored-in markings previously explained as a further possible application there is the fundus perimetry. In this case the markings serve as so-called stimuli, which the patient recognizes or in the event of field-of-view failures does not recognize. It is particularly advantageous if an infrared laser is employed as the source of the observation light as thereby the observation light does not have an adverse effect on the recognition of the stimuli. By means of this embodiment of an apparatus for observing the rear portions of the eye, a fundus perimeter is yielded that makes microperimetry possible under visual control and moreover also permits training the eye to eliminate vision or fixation weaknesses.

In microperimetry it is also advantageous, however, not only when the present invention is employed, if additional illumination of the surrounding area is provided, which, by way of illustration, is coupled via a semitranslucent mirror. This illumination of the surrounding area permits, for example, perimetry of a "specific level of lightness", but, of course, has other advantages.

In fundus perimetry, special search algorithms, scotoma detection, a variable measuring point density, fundus tracking for automatic detection of the position of the projected markings on the fundus can be realized via a control unit. Furthermore, a positive and negative perimetry, color differential examinations, etc. may be carried out.

A further improvement, in accordance with the present invention, of an apparatus, which is particularly suited for the observation of the rear portions of the eye, is provided with one or several detectors, before which shutters are arranged in such a manner that the result a dark field illumination of the detectors so that only the multiply scattered components are recorded in the image of the object or the fundus. By this means an intensified contrast representation of specific structures, e.g. papillary tissue, is made possible, which is of utmost interest for automatic determination of the edge of the papilla within the scope of glaucoma diagnosis.

By providing several detectors it is, of course, also possible to receive "dark-field" and "light-field" images simultaneously.

Furthermore, in accordance with the present invention it is advantageous if earlier received images and/or markings are mirrored congruently into the received and presented image in such a manner that the operating personnel, by way of illustration, can compare images made according to a different method, such as angiographs, or control an automatic laser beam positioning. To this point, reference is again made to the German patent application P 36 07 721.6. The "mirroring in" can occur by optical means; preferably, however, by electronic means in the observation apparatus, such as by means of a monitor.

The apparatus of the present invention is not only suited as an image-producing or diagnostic device, but also as a processing or therapy device and can be combined with many very different instruments, such as processing or treatment lasers of different wavelengths.

In particular, however, it is advantageous if in addition the beam of a coagulating laser, e.g. an $Ar^-$-laser or a dye laser, is mirrored in preferably between the scanning device and the eyeball. However, "a short" raising of the output of the observation laser is, of course, also possible for coagulating as described in U.S. Pat. No. 4,213,678. The joint implementation of the "scanning device" permits in this case in particular treating large areas or several areas in one step.

An apparatus for observing the rear portions of the eye with a scanning illumination is particularly useful as an image transmitter for a so-called eye tracking unit due to its reflex-free and high resolution presentation of the image. With regard to the principal eye-tracing-concept-directing of the observation and/or treatment unit, switching off the laser in the event of eye motion, etc. reference is again made to the German patent application P 36 07 721.6, the content of which, moreover, is expressly viewed as a disclosure of this application.

Furthermore, an apparatus for observing the rear portions of the eye with a scanning illumination is especially suited as an image transmitter for treatment planning due to its reflex-free and high resolution presentation of the image as also already described in the German patent application P 36 07 721.6.

It is especially advantageous, however, to employ an apparatus with "double scanning", in contrast to the apparatus known from EP-A-0 145 563, a field-of-view shutter having a diameter from 80 to 150 $\mu$m is used, being thus substantially larger than the diameter of the point image on the fundus of the eye which is typically between 8 and 12 $\mu$m and at the most, however, approx. 20 $\mu$m. This selection of field-of-view shutter, which differs from the selection in EP-A-0 145 563, particularly supports the concept of the present invention of using several individual detectors. The pupil separation in the pupil plane may be carried out in a state of the art manner from the above-mentioned individual references.

BRIEF DESCRIPTION OF THE DRAWING

The present invention is made more apparent from the following detailed description of preferred embodiments when taken in conjunction with the accompanying drawings wherein.

DETAILED DESCRIPTION OF THE DRAWINGS

Figure 1:
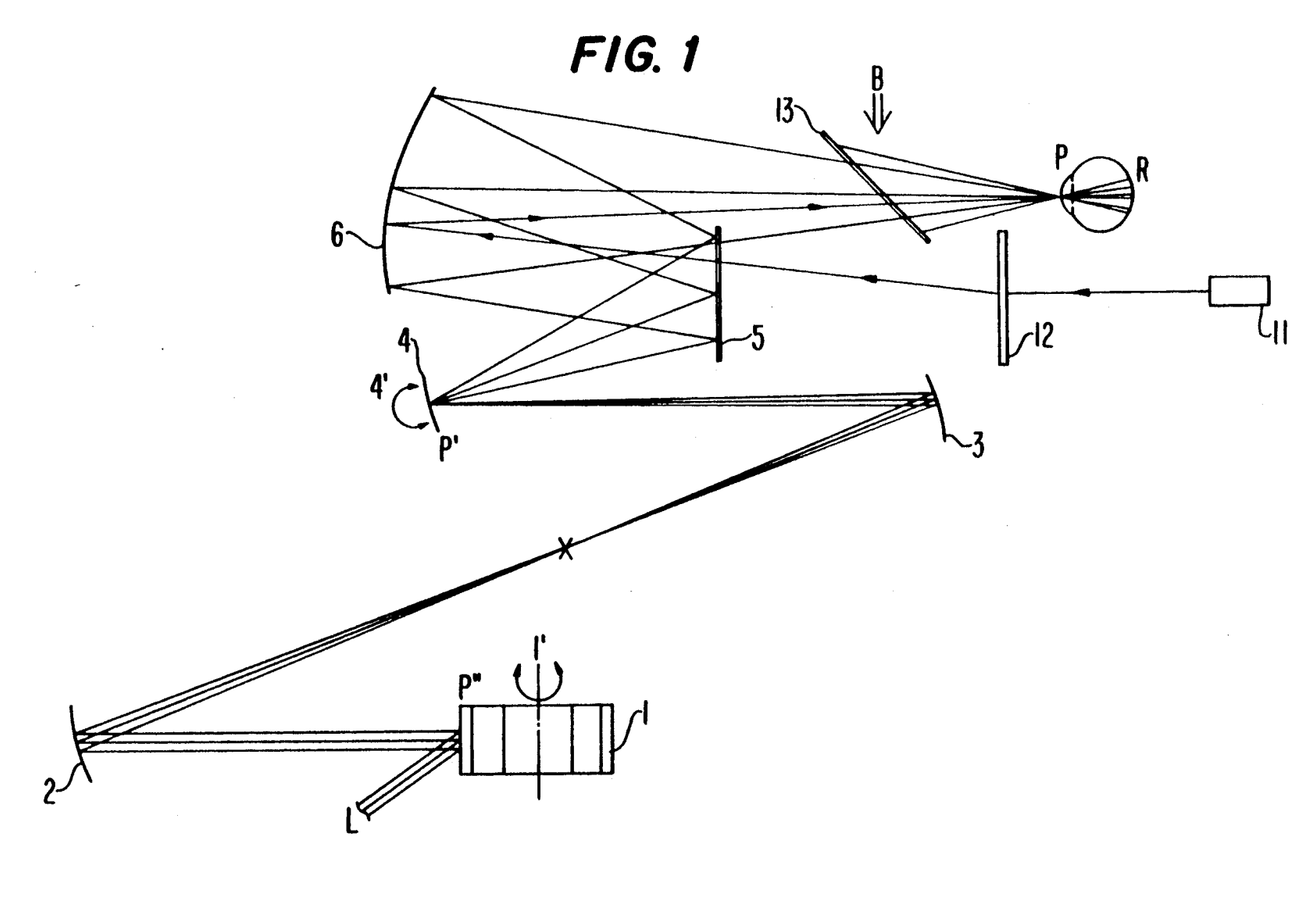
FIG. 1 illustrates the general beam path of an apparatus in accordance with the present invention.

FIG. 1 shows the general beam path of an apparatus of the present invention using, for illustration purposes and without limiting the scope of the invention, a laser scanning opthalmoscope. Light L of an illumination device illustrated in more detail in FIG. 2 hits a polygonal mirror 1 of a scanning device. The polygonal mirror 1 deflects light L in a horizontal direction corresponding to its shift in the direction of an arrow 1'. A concave mirror 2 and another concave mirror 3 reflect the image of the horizontally deflected bundle of light onto a galvanometer mirror 4, which swings in the direction of an arrow 4' and additionally deflects the bundle of light in a vertical direction. The bundle of light deflected in a horizontal direction (x) and in a vertical direction (y) is deflected by a plane mirror 5 and focussed by a concave mirror 6 onto the fundus (retina) R of an eyeball 7 in such a manner that the light beam scanning in the x and y directions has a "waist" in the pupil plane P of the eyeball 7. The refractive power of elements 2, 3, and 6, as well as the optical paths between the elements, are measured in such a fashion that the planes P' or P" of mirror 4 or 1 are planes conjugate to the pupil plane P of eyeball 7.

Figure 2:
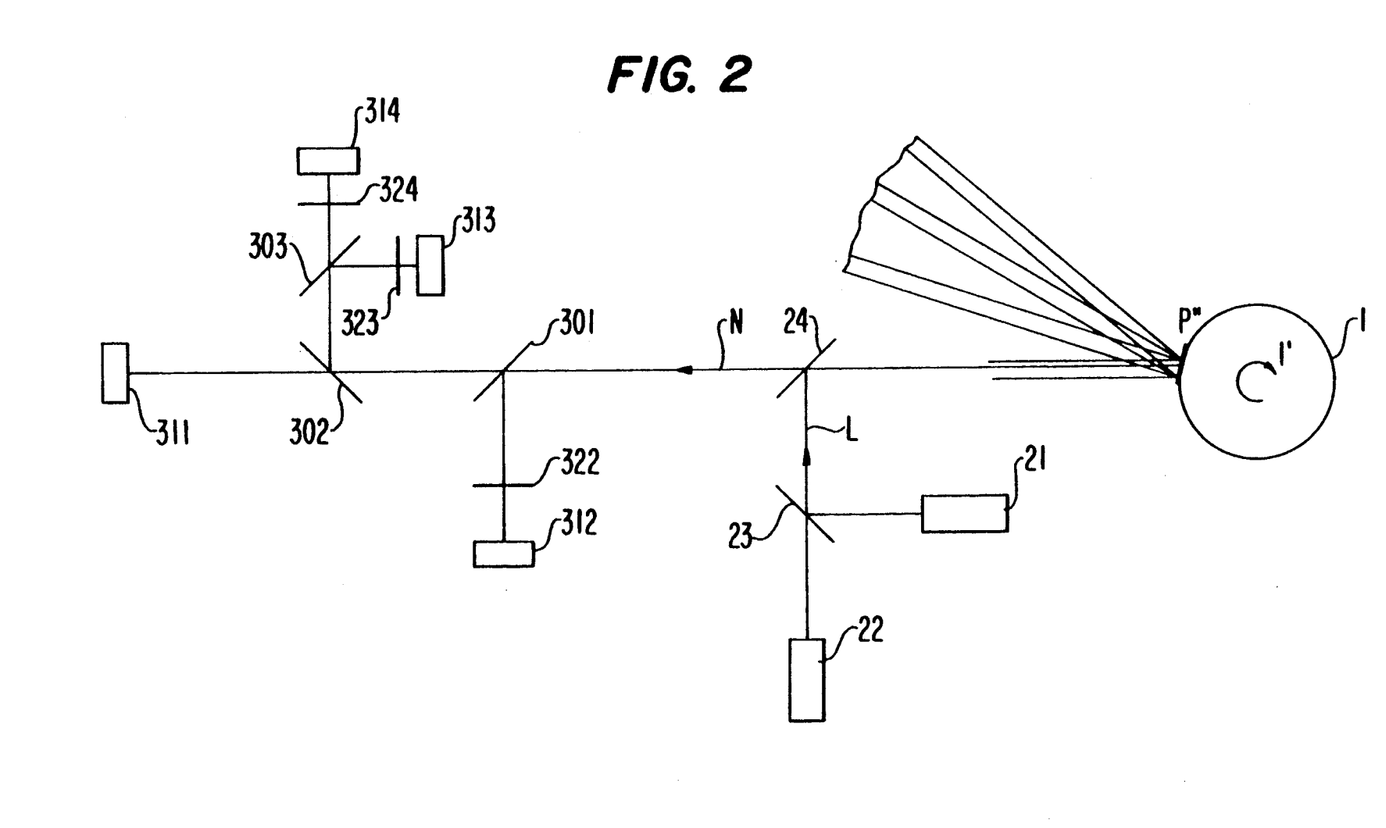
FIG. 2 illustrates the beam path "before" the scanning device.

The light N reflected or scattered from the fundus of the eye R is guided back on the reverse path via mirrors 6, 5 4, 3 and 2 to the polygonal mirror 1 and may, as illustrated in more detail in FIG. 2, be detected "behind" the scanning device by a stationary arrangement of detectors.

Furthermore, an independent source of light 11, which preferably is a laser, and a deflection unit 12, operating independently of deflection device 1,4, are provided to deflect beam M of light source 11 and permit positioning beam M on the retina. For this purpose, mirror 5 in the illustrated embodiment is designed as a semitranslucent mirror.

Light source 11 may, by way of illustration, be a coagulation laser, thus e.g. an Ar$^-$-laser, an image mark transmitter or the light source permitting conducting a microfundus perimetry.

Deflection unit 12 may, of course, be any unit which permits positioning a light beam on a surface of the object. Deflection unit 12 may be an acousto-optical deflector or a wobble unit.

Moreover, another semitranslucent mirror 13, which permits expansive mirroring in of light B from an additional source of illumination, which is not depicted, is arranged in the beam path. The purpose of light B is to illuminate the fundus of the eyeball R and may, particularly in the case of microperimetry, serve to "set" a specific light level on which subsequently the marks mirrored in with laser 11 must be recognized.

FIG. 2 shows the design of the illumination apparatus and the detector device arranged "before" or "behind" the polygonal mirror 1 of the scanning device.

In the depicted preferred embodiment the illumination device is provided with two lasers 21 and 22, which emit light of different wavelengths, by way of illustration in the UV and visible range or in the visible and infrared range. The light paths of both lasers are united by means of a semitranslucent or wavelength-selective mirror 23 and coupled by a divider mirror 24 in the mutual light path of the illumination light L and the detection light N.

The design of the divider mirror 24 determines the design of the entrance pupil, i.e. of the part of the pupil of the eye passed through by the illumination light L, and the exit pupil, i.e. the part of the pupil of the eye passed through by the light N reflected or scattered from retina R.

Figure 5:
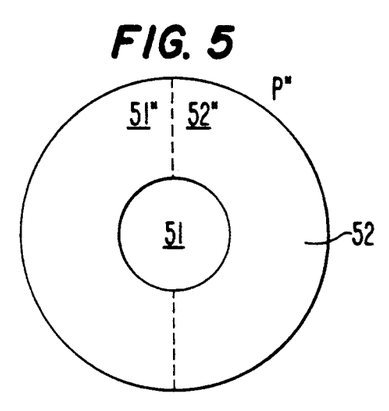
FIG. 5 illustrates possible pupils for the illumination light and the reflected light.

FIG. 5 depicts a possible pupil separation. By means of a wavelength-selective coating of the divider mirror 24, it can be achieved that the light from, for example a laser operating in the visible range is only reflectd by the region surrounding the optical axis in such a manner that the entrance pupil is the region 51.

The region 52 surrounding region 51 is then the exit pupil. If the mirror layers of mirror 24 are selected in such a fashion that the layer reflecting visible light is translucent to, by way of illustration, light in the infrared range and reverse, the entrance pupil for light in the infrared range is region 52 and region 51 is the exit pupil.

Due to the different angles of the peripheral beams, the light passing region 51 is focused on retina R with a great depth of focus, whereas the light entering through region 52 is focused with a small depth of focus. In this manner images having great depth of focus and images having little depth of focus in the range from 0.1 mm and under, which permit a depth analysis, can be received simultaneously with two lasers 21 and 22, whereby the simultaneously received image with great depth of focus makes a full overall representation possible.

Furthermore, FIG. 5 indicates that the exit pupil 51 may be separated into two regions 52' and 52". The difference between the signals received in the regions 52' and 52" permit drawing conclusions about the directional asymmetry of the transverse scattering.

Moreover, FIG. 2 shows, by way of example, a detector device employed in accordance with the present invention. The detector device is provided with four individual detectors 311, 312, 313 and 314, arranged in a plane conjugate to the retina R and hit by the detection light N reflected from the retina R.

Figure 4A:
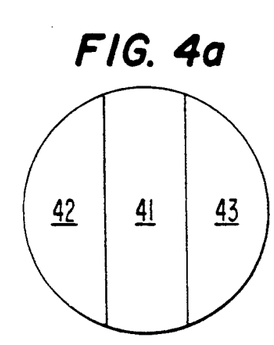
FIG. 4a-c illustrate possible arrangements of detectors in a plane conjugate to the pupil.
Figure 4B:
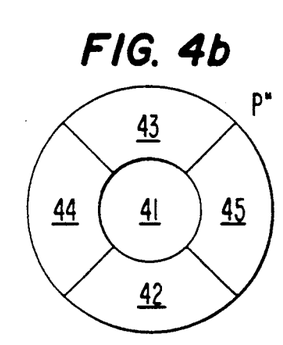
Figure 4C:
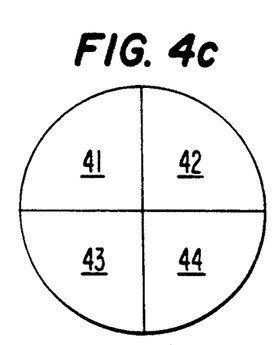

Due to the "scan processing" employed for the image build-up, detecting all the scattered or reflected light in the assessable space angle and using it time-sequentially for building up the image, the detectors do not have to actually be physically arranged in a plane conjugate to the retina, but rather it suffices if field-of-view-determining shutters are arranged in this plane (or in FIG. 4 in a plane conjugate to the pupil) and the light passing through these shutters is directed by elements transmitting an intermediate representation, by way of illustration a relay optic or light conductor, to the spaced detectors. Whenever detectors are mentioned in the following discussion, it is also meant that field-of-the-view-determining shutters may be substituted instead.

Furthermore, according to FIG. 2, beam dividers 301, 302 and 303 may be provided. There is element influencing the beam path arranged before detector 311, whereas a 0> analyzer 322 is arranged before detector 312, a 45> analyzer 323 is arranged before detector 323 and a quarter-wave plate 324 is arranged before detector 314.

If the output signals of detectors 311 to 314 are designated A-D, the Stokes parameter $S_i$ may be formed to analyze the polarization state of the reflected light by means of a synchronizer (not shown) and evaluation unit:

$$S = A, S_1 = B - A, S_2 = C - A, S_3 = D - A$$

Therefrom the following quantities may be derived to describe the polarization characteristics:

$$\text{Degree of polarization} \quad P = \sqrt{(S_1^2 + S_2^2 + S_3^2)}/S$$

$$\text{Direction of polarization} \quad \tan 2\phi = S_2/S_1$$

$$\text{Ellipticity} \quad \sin 2\gamma = S_3/\sqrt{(S_1^2 + S_2^2 + S_3^2)}$$

The determination of the polarization characteristics permits determining and making anisotropic, e.g. directed structures of the retina prominent, such as for example the nerve fiber layer.

The detector arrangement (shutter arrangement) illustrated in FIG. 2 is merely an example of a detector arrangement implemented in accordance with the present invention, in which several detectors arranged in a plane conjugate to the object to be imaged, which in the present example of an embodiment is the retina.

Figure 3:
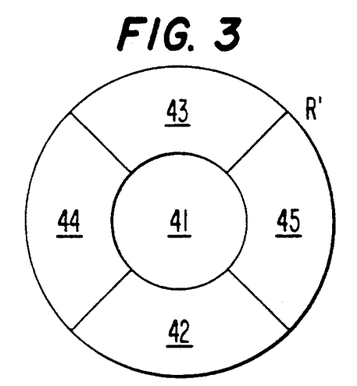
FIG. 3 illustrates a possible arrangement of detectors in a plane conjugate to the object.

FIG. 3 shows another example of a detector arrangement (or arrangement of field-of-view-determining shutters) having detectors 41 to 45 in a plane conjugate to the plane of the retina. Detector 41 is a so-called light-field detector, whereas detectors 42 to 45 are dark-field detectors. If the ouput signals of detectors 41 to 45 are designated 41' to 45', the quantity $(41'+43')-(44'+45')$ indicates the directional characteristics of the reflexion.

Of course, it is also possible to arrange the detectors or field-of-view-determining shutters not in planes conjugate to the object plane R, but, by way of illustration in planes conjugate to pupil P. Corresponding examples are shown in FIGS. 4a to 4c.

FIG. 4a depicts a detector arrangement having three detectors 41 to 43. The output signal from detector 41 is proportional to the specular portion, whereas the output signals 42' and 43' from detectors 42 and 43 represent the scattering under large angles.

FIG. 4b depicts a detector arrangement having five individual detectors 41 to 45 arranged in a plane conjugate to pupil plane P in a confocal design. Output signal 41' from detector 41 indicates again the specular portion, whereas output signals represent (42'−43') the diff. phase contrast and output signals (42'−43')−(44'+45') the scattering characteristics.

FIG. 4c shows a detector arrangement, having four circle sector-shaped individual detectors 41 to 44, again arranged in a plane conjugate to pupil P. The coupling (41'+43')−(42'+44')

of the output signals from these detectors represents, by way of illustration, the left-right asymmetry of the scattered light. Once more it is pointed out that the aforegoing detector arrangement and arrangement of field-of-view-determining shutters have been used synomymously.

The present invention has been described above using preferred embodiments without the intention of limiting the scope of the overall inventive concept—to gain essential ground-laying information about the object to be imaged, e.g. the fundus of the eye by special types of illumination and/or the analysis of the light scattered back according to most varied criteria than is possible with any other known apparatus for producing images.

Most varied modifications and alterations are, of course, possible within the scope of this overall inventive concept.

The optical image pre-processing of the present invention may also be made more sophisticated by specially designed exchangeable and/or variable shutters, like LCD shutters before the detectors, instead of or in addition to elements 322 to 324.

The apparatus may also operate without "double scanning, in particular with the detector arrangements arranged in the pupil plane, which can forego confocal detection.

Apparatus having only one detector, but correspondingly designed shutters are also possible. Field-of-view-determining shutters, arranged in an exchangeable manner in a specific plane may also be connected via light conducting means to stationary detectors arranged in another plane.

The mirroring-in of a positionable additional beam and/or of the surrounding illumination may also be carried out in another manner than as previously described. Other pupil separations or strict confocal arrangements may also be realized.

The preceding description of the present invention permits realizing the assessment and synchronization unit, which couples and/or stores the individual signals, e.g. a microcomputer, even without a detailed description of an embodiment.

The preceding description of a laser-scanning opthalmoscope does not restrict the basic concept of the present invention to opthalmoscopes, although they, in particular, are especially advantageous for the observation of the fundus of the eye due to the specific difficulties resulting from the pupil of the eye. The basic inventive concepts may, of course, be employed in other instruments, including those employed for the observation of the cornea, designed for medical and technical use as laser-scanning cameras or laser-scanning microscopes or in other laser-scanning-image transmitters.

The preceding description is to be construed as an illustration and not a restriction or renouncement of protection of elements of invented further embodiments claimed in the individual claims hereto of state of the art apparatuses.

I claim:

1. An apparatus for producing images of an object, comprising an illumination device, the light of which is focused on the object to be imaged and which is provided with at least one laser; a scanning device which produces a scanning motion of the light from said illumination device on said object to be imaged; a detector device having at least one detector which receives the light reflected from said object to be imaged; and an assessment and synchronization unit which produces the image from a time-sequential output signal from said detector device comprising individual detectors arranged conjugate to one of different planes and to different regions of a plane one of shutters and polarization filters being arranged at selected detectors for selective reception of light reflected from different planes, areal distribution of the intensity of said light in a particular plane and a polarization state of said light.

2. An apparatus according to claim 1, wherein said illumination device projects light of several wavelengths simultaneously onto said object to be imaged (R), and for the light of each wavelength at least one a wavelength-selective individual detector is provided.

3. An apparatus according to claim 2, wherein the entrance and/or exit pupils of the light beams of differing wavelengths are different.

4. An apparatus according to claim 3, wherein the representations by said light of differing wavelengths have differing depths of focus.

5. An apparatus according to claim 1, wherein said assessment unit presents the output signals from said individual detectors on one or several monitors.

6. An apparatus according to claim 1, wherein said assessment unit couples said output signals from said individual detectors in real time and presents the coupled signal on a monitor.

7. An apparatus according to claim 1, wherein said assessment unit feeds said output signals from said individual detectors into an image memory and couples the stored signals.

8. An apparatus according to claim 1, wherein said detector device receives said light reflected from said object to be imaged via said scanning device and, selective shutter devices are provided.

9. An apparatus according to claim 1, wherein a detector arrangement, which determines the distribution of the intensity of said reflected light, is provided in a plane conjugate to the pupil (P) of the eye for observing the fundus of the eye.

10. An apparatus according to claim 9, wherein said assessment unit determines from said output signals from said individual detectors characteristic features of said distribution of intensity, including the main point of said reflected light and directional asymmetries.

11. An apparatus according to claim 10, wherein said individual detectors are sectors of a circle and are arranged in a circle.

12. An apparatus according to claim 1, wherein a detector arrangement is provided in a plane conjugate to said object to be imaged, which determines the distribution of intensity of said reflected light in said plane.

13. An apparatus according to claim 12, wherein said assessment unit determines from said output signals from said individual detectors the characteristic features of said distribution of intensity including transverse scattering within the retina.

14. An apparatus according to claim 1, wherein a number of individual detectors, before which analyzers are provided in a plane conjugate to said object to be imaged.

15. An apparatus according to claim 14, further comprising four individual detectors, wherein no optically effective element is arranged before the first individual detector, a first linear analyzer is arranged before the second individual detector, a second linear analyzer turned 45° to said first analyzer is arranged before the third individual detector, and a quarter-wave plate is arranged before the fourth individual detector, and
said assessment unit determines the degree of polarization, the polarization direction and the ellipicity from the output signals.

16. An apparatus according to claim 1, wherein before said detector device are connected at least partially structured filters and/or variable shutters.

17. An apparatus according to claim 16, wherein areal light modulators, which can be triggered electronically, from said filters.

18. An apparatus according to claim 17, wherein said light modulators are LCD elements having regions, which can be triggered separately.

19. An apparatus according to claim 16, wherein said filters can be shifted or turned in a longitudinal direction and/or oblique to the detection beam path.

20. An apparatus according to claim 1, wherein, in addition, markings can be projected onto said fundus of the eye.

21. An apparatus according to claim 20, wherein said projection of said markings occurs by modulation of said illumination light.

22. An apparatus according to claim 21, wherein at least one of an additional source of light and an additional deflection unit is provided for said projection of said markings.

23. An apparatus according to claim 22, wherein said deflection unit is provided with one of an acousto-optical demodulator and a wobble unit.

24. An apparatus according to claim 20, wherein said projection of said marks occurs for the purpose of fundus perimetry.

25. An apparatus according to claim 1, wherein said scanning device is an x/y scanning device which is provided with a rotatable polygonal mirror drum and a galvanometer mirror.

26. An apparatus according claim 1, wherein for the illumination of the surrounding area an additional light source is provided, the light (B) of which expansively illuminates said object to be imaged.

27. An apparatus according to claim 1, wherein the beam of an operational laser is additionally mirrored in.

28. An apparatus according to claim 1, wherein a control unit is configured to redirect at least one of an observation beam path and an operational laser beam and to selectively switch off the laser.

29. An apparatus according to claim 28, wherein said control unit additionally permits setting the operational parameters including treatment planning.

30. An apparatus according to claim 1, wherein a field-of-view shutter, which produces a dark-field illumination for at least one part of said individual detectors, is arranged before said detector device.

31. An apparatus according to claim 1, wherein at least one of a fundus angiograph and markings can be congruently superimposed on the received image.

32. An apparatus according to claim 1, wherein said control unit is provided with an image processing device for processing the images received simultaneously or consecutively.

33. An apparatus according to claim 1, wherein said illumination device, said scanning device and said detector device form a confocal arrangement and said field-of-view shutters of at least some of said individual detectors are substantially larger than the diameter of the image point on said fundus of the eye.

34. An apparatus according to claim 1, wherein field-of-view-determining shutters and their detectors are arranged spaced and stationary in planes conjugate to said differing planes.

35. An apparatus according to claim 34, wherein light conducting means connect said shutters and said detectors.

36. An apparatus for producing images of an object and for observing the rear portions of the eye, comprising
- an illumination device, the light of which is focused on the object to be imaged and which is provided with at least one laser wherein said illumination device projects light of several wavelengths simultaneously onto said object to be imaged (R), and for the light of each wavelength at least one and a wavelength-selective individual detector is provided;
- a scanning device, which produces a scanning motion of the light from said illumination device on said object to be imaged;
- a detector device, having at least one detector, which receives the light reflected from said object to be imaged; and
- an assessment and synchronization unit which produces the image from the time-sequential output signal from said detector device.

37. An apparatus according to claim 36, wherein before said detector device are connected at least partially structured filters and/or variable shutters.

38. An apparatus according to claim 36, wherein markings can be projected onto said object to be imaged and onto said fundus of the eye.

39. An apparatus according to claim 36, wherein for the illumination of the surrounding area an additional light source is provided, the light of which expansively illuminates said object to be imaged and in particular said fundus of the eye.

40. An apparatus according to claim 36, wherein the beam of an operation coagulation laser is additionally mirrored in.

41. An apparatus according to claim 36, wherein a control unit is configured to redirect at least one of an observation beam path and an operational laser beam and to selectively switch off the laser.

42. An apparatus according to claim 36, wherein a field-of-view shutter is arranged before said detector device to produce a dark-field illumination for said individual detectors.

43. An apparatus according to claim 36, wherein a fundus angiograph and/or markings can be congruently superimposed on the received image.

44. An apparatus according to claim 36, wherein said control unit is provided with an image processing device for processing the images received simultaneously or consecutively.

45. An apparatus for producing images of an object and for observing rear portions of an eye, comprising:
- an illumination device whose light is focused on an object to be imaged and which is provided with at least one laser;
- a scanning device operatively arranged to produce a scanning motion of the light from said illumination device on the object to be imaged;
- a detector device having at least one detector receiving light reflected from the object to be imaged;
- an assessment and synchronization unit producing the image from a time-sequential output signal from said detector device; and
- at least one of partially structured filters and variable shutters connected before said detector device so as to detect intensity distribution of the light reflected at the fundus of the eye.

46. An apparatus for producing images of an object and for observing rear portions of an eye, comprising:
- an illumination device whose light is focused on an object to be imaged and which is provided with at least one laser;
- a scanning device operatively arranged to produce a scanning motion of the light from said illumination device on the object to be imaged;
- a detector device having at least one detector receiving light reflected from the object to be imaged;
- an assessment and synchronization unit producing the image from a time-sequential output signal from said detector device; and
- an additional light source configured to illuminate a surrounding area, such that the light of the additional light source expansively illuminates a fundus of the eye for effecting fundus perimetry.

* * * * *